(12) United States Patent
Townley

(10) Patent No.: US 6,626,949 B1
(45) Date of Patent: Sep. 30, 2003

(54) DIAMOND COATED JOINT IMPLANT

(75) Inventor: Charles O. Townley, Port Huron, MI (US)

(73) Assignee: BioPro, Inc., Port Huron, MI (US)

( * ) Notice: Subject to any disclaimer, the term of this patent is extended or adjusted under 35 U.S.C. 154(b) by 0 days.

(21) Appl. No.: 09/615,268

(22) Filed: Jul. 13, 2000

Related U.S. Application Data

(60) Provisional application No. 60/143,708, filed on Jul. 14, 1999.

(51) Int. Cl.$^7$ ................................................. A61F 2/30
(52) U.S. Cl. ................................. 623/23.39; 623/18.11
(58) Field of Search .......................... 623/23.39–23.43, 623/18.11–23.14

(56) References Cited

U.S. PATENT DOCUMENTS

| | | | | |
|---|---|---|---|---|
| 2,934,065 | A | * 4/1960 | Townley ................... | 623/23.14 |
| 3,745,623 | A | * 7/1973 | Wentorf, Jr. et al. ........... | 29/95 |
| 4,522,680 | A | 6/1985 | Ogawa ........................ | 156/624 |
| 4,681,640 | A | 7/1987 | Stanley ....................... | 148/1.5 |

(List continued on next page.)

FOREIGN PATENT DOCUMENTS

| | | | | |
|---|---|---|---|---|
| GB | 0 302 717 | * | 2/1989 | ............. A61F/2/30 |
| WO | WO 95/20253 | | 7/1995 | |

OTHER PUBLICATIONS

Abraham, *Mat. Tech.*, vol. 11, No. 5, 1996, pp. 199–200, "Spurt of Activities in Diamond and Diamond–Like Films."

Browne, *The New York Times*, Mar. 12, 1996, pp. B5 & B10, "Lucky Lab Accident Yields New Recipe for Diamond Coating."

Collection, miscellaneous covers, comments (various journals).

Lorincz, *Tooling & Production*, Nov. 1995, pp. 37 et seq., "Diamond Coatings Sparkle."

Mistry et al., *Innovations in Materials Research*, vol. 1, No. 2, 193–207, 1996, "A Revolutionary Diamond Synthesis Technique: The QQC Materials Deposition Process."

(List continued on next page.)

Primary Examiner—Corrine McDermott
Assistant Examiner—Thomas Barrett
(74) Attorney, Agent, or Firm—Christopher John Rudy

(57) ABSTRACT

A joint implant, which is not itself a femoral component for a conventional hip joint replacement prosthesis having a diamond or diamond like coated ball, has a diamond or diamond like coated articulating surface. The coating can be transitional in nature. The implant can be based on a suitable support material, for example, a metal, a ceramic, or a plastic, with the support material being coated with the diamond or diamond like substance. The implant may be, for instance, for a ginglymous type, an enarthrodial type, or a digital joint. Convex and/or concave articulating surface(s) of a prosthesis can have the coating.

22 Claims, 2 Drawing Sheets

OTHER PUBLICATIONS

Figure 6:
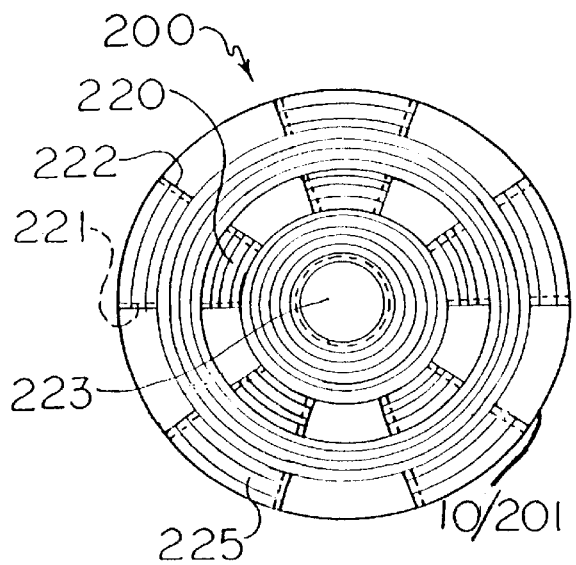

| | | | | |
|---|---|---|---|---|
| 4,701,592 | A | | 10/1987 | Cheung ................ 219/121 LT |
| 4,840,630 | A | * | 6/1989 | Kitamura ................. 623/22.13 |
| 4,849,199 | A | | 7/1989 | Pinneo ....................... 423/446 |
| 4,874,596 | A | | 10/1989 | Lemelson ................... 423/446 |
| 4,892,751 | A | | 1/1990 | Miyake et al. ................ 427/34 |
| 4,948,629 | A | | 8/1990 | Hacker et al. ............. 427/53.1 |
| 4,954,365 | A | | 9/1990 | Neifeld ...................... 427/53.1 |
| 4,981,717 | A | | 1/1991 | Thaler ....................... 427/53.1 |
| 4,986,214 | A | | 1/1991 | Zumoto et al. ............. 118/722 |
| 4,987,007 | A | | 1/1991 | Wagal et al. .............. 427/53.1 |
| 5,017,317 | A | | 5/1991 | Marcus ........................ 264/81 |
| 5,066,515 | A | | 11/1991 | Oshawa ..................... 427/53.1 |
| 5,080,752 | A | | 1/1992 | Kabacoff et al. ........... 156/603 |
| 5,080,753 | A | | 1/1992 | Doll et al. .................. 156/609 |
| 5,094,915 | A | | 3/1992 | Subramaniam ............. 428/408 |
| 5,096,740 | A | | 3/1992 | Nakagama et al. ........ 427/53.1 |
| 5,098,737 | A | | 3/1992 | Collins et al. ............. 427/53.1 |
| 5,130,111 | A | | 7/1992 | Pryor ......................... 423/446 |
| 5,139,591 | A | | 8/1992 | Doll et al. .................. 156/609 |
| 5,154,945 | A | | 10/1992 | Baldwin et al. ........... 427/53.1 |
| 5,163,961 | A | * | 11/1992 | Harwin ................... 623/22.46 |
| 5,176,788 | A | | 1/1993 | Kabacoff et al. ........... 156/603 |
| 5,236,545 | A | | 8/1993 | Pryor ......................... 156/613 |
| 5,236,637 | A | | 8/1993 | Hull ............................ 264/22 |
| 5,247,180 | A | | 9/1993 | Mitcham et al. ......... 250/492.1 |
| 5,248,456 | A | | 9/1993 | Evans, Jr. et al. ............ 264/22 |
| 5,256,340 | A | | 10/1993 | Allison et al. ................ 264/22 |
| 5,260,009 | A | | 11/1993 | Penn .......................... 264/40.1 |
| 5,273,788 | A | | 12/1993 | Yu .............................. 427/554 |
| 5,370,700 | A | * | 12/1994 | Sarkisian et al. ............. 623/20 |
| 5,516,500 | A | | 5/1996 | Liu et al. .................... 423/446 |
| 5,554,415 | A | | 9/1996 | Turchan et al. .......... 427/248.1 |
| 5,593,445 | A | * | 1/1997 | Waits ...................... 623/23.42 |
| 5,620,754 | A | | 4/1997 | Turchan et al. ............. 427/554 |
| 5,635,243 | A | | 6/1997 | Turchan et al. ............. 427/248 |
| 5,643,641 | A | | 7/1997 | Turchan et al. ............. 427/595 |
| 5,645,601 | A | * | 7/1997 | Pope et al. .................... 623/18 |
| 5,648,127 | A | * | 7/1997 | Turchan et al. ............. 427/596 |
| 5,702,469 | A | * | 12/1997 | Whipple et al. ......... 623/21.15 |
| 5,731,046 | A | | 3/1998 | Mistry et al. ................ 427/553 |
| 5,766,257 | A | * | 6/1998 | Goodman et al. ........ 623/20.21 |
| 5,900,225 | A | | 5/1999 | Mistry et al. ................ 423/446 |
| 5,981,827 | A | * | 11/1999 | Devlin et al. .................. 623/16 |
| 6,136,034 | A | | 10/2000 | Townley ................... 623/22.23 |
| 6,302,916 | B1 | * | 10/2001 | Townley et al. ......... 623/23.58 |

OTHER PUBLICATIONS

Mistry et al., *Mat. Res. Innovat.*, vol. 4, pp. 149–156, 1997.

QQC, Inc., "Brilliant Discovery," Jan. 2, 1999.

QQC, Inc., "Commitment to the Aluminum Processing Industry."

Shapley, *Financial Times*, Sep. 3, 1996, "Cutting Edge, Synthetic Diamonds Get Cheaper."

Society of Manufacturing Engineers, *Manufacturing Engineering*, Feb., 1995, "Diamond Coatings: Ready to Rip?".

Townley, U.S. provisional patent application No. 60/143,708 filed on Jul. 14, 1999 (specification).

Townley, U.S. utility patent application No. 09/148,842 filed on Sep.4, 1998 (specification).

Townley, U.S. utility patent application No. 09/160,746 filed on Sep. 25, 1998 (specification).

Townley, U.S. utility patent application No. 09/352,472 filed on Jul. 14, 1999 (specification).

Turchan, "Introducing QQC, Inc.," 1995.

Van Belle, *Photonics Spectra*, Apr. 1999, pp. 56 et seq., "Lasers: A Diamond Coating's Best Friend."

Weiss, *Unidentified Journal*, Jun. 1996, "Lasers Make Fast Diamond Films."

* cited by examiner

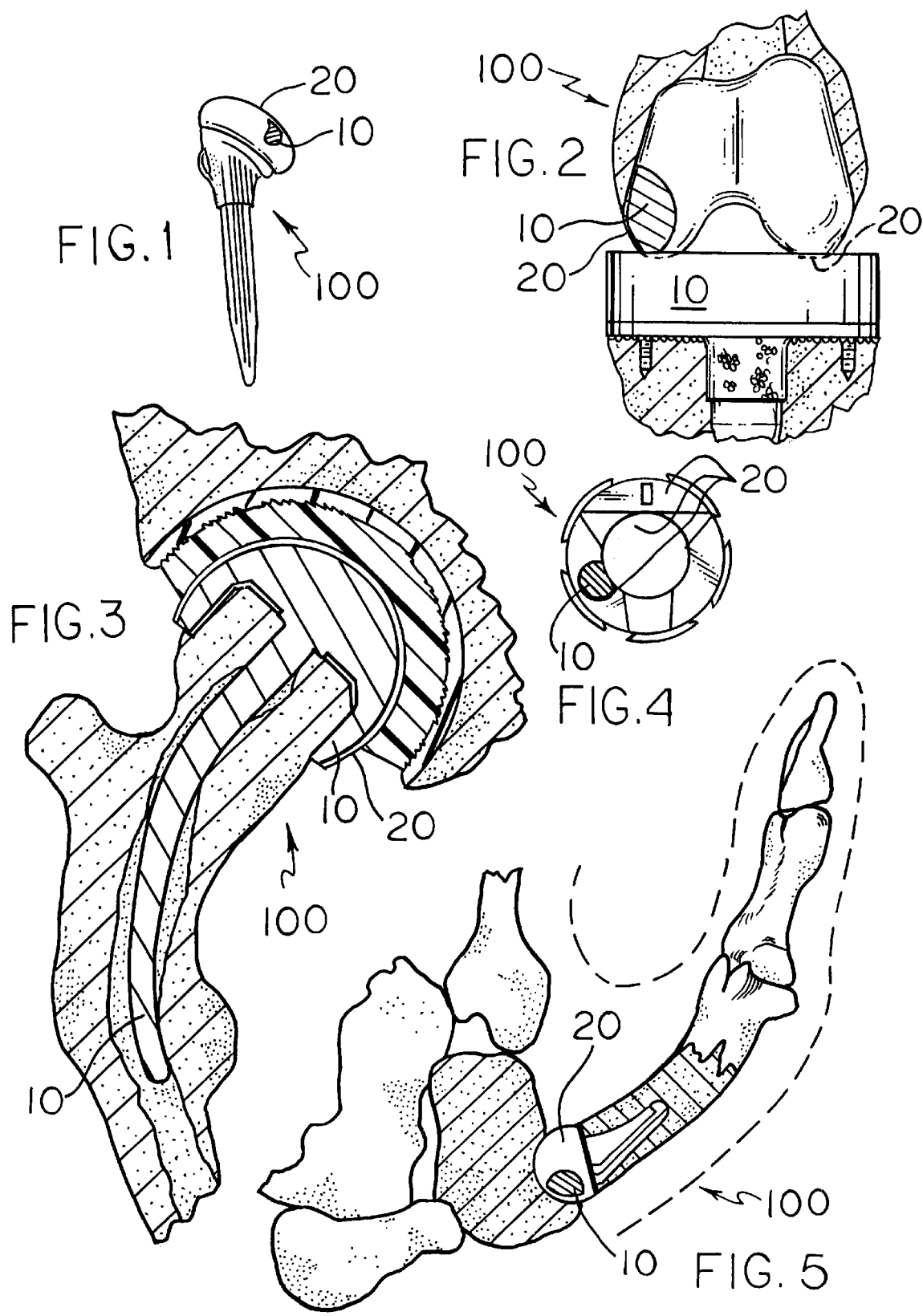

DIAMOND COATED JOINT IMPLANT

CROSS-REFERENCE CLAIM OF DOMESTIC PRIORITY

This claims benefit under 35 USC 119(e) of U.S. provisional patent application No. 60/143,708 filed on Jul. 14, 1999 A.D. The specification of the '708 application is incorporated herein by reference.

BACKGROUND TO THE INVENTION

I. Field of the Invention

The present invention concerns joint implants with diamond coated surfaces, which, in general, are useful in arthroplasty.

II. Prior Art and Problems

In the field of mechanical devices such as moving automotive and truck components it is known to diamond coat certain metal mechanical bearing surfaces. This increases their hardness and, in turn, may provide for a more friction free, longer wearing part.

In the pertinent general field of joint implants for human beings or animals, current technology includes use of a metal or ceramic ball which articulates upon a polyethylene cup, for example, of ultra high molecular weight polyethylene (UHMWPE). However, asperities on the ball component surface accelerate the loss of the polyethylene, which has been reported to be a major cause in osteolytic bone loss, with loosening and subsequent failure of the joint implant. Smoother ceramic may be employed in place of the relatively rougher metal to attempt to ameliorate the problem and provide a better joint articulation. Ceramic, however, has its own difficulties, including the requirement that more of the ceramic relative to metal must be employed to keep the ceramic part from cracking, i.e., relative bulkiness, and the proclivity of the ceramic to break, which results in more bone having to be resected, rather than being saved. Also, ceramic, although known generally to provide for a smoother surface than metal, is not entirely free from debris-causing asperities.

Certain diamond or diamond like coating methods have been disclosed, however, to be useful in making not only the metal mechanical bearing surfaces but replacement joints such as the replacement ball of a hip joint prosthesis. See, e.g., Turchan et al., U.S. Pat. Nos. 5,554,415; 5,635,243; 5,643,641; and 5,648,127. See also, QQC, Inc., WO 95/20253 (Jul. 27, 1995); *Mfg. Eng.*, "Diamond Coatings, Ready to Rip?" (February 1995); and Mistry et al., *Mat. Res. Innovat.*, 1:149–156 (1997).

It would be desirable to address and improve upon the same.

SUMMARY OF THE INVENTION

The present invention provides a diamond or diamond like coated joint implant which in general is not a femoral component for a conventional hip joint replacement prosthesis having a diamond or diamond like coated ball. The implant can be based on a metal or other suitable support material, to include, say, ceramic and plastic, which is coated with a diamond or diamond like substance, and so forth and the like, and can include heads or other convex articulating surfaces and/or sockets or other concave articulating surfaces, say, in ginglymous or enarthrodial type joints, and so forth. Beneficially, the coating is transitional in nature.

The invention is useful in arthroplasty.

Significantly, by the invention, an articulating surface of superior hardness and smoothness can be provided. Accordingly, the level of asperity-related wear debris, and the osteolytic loosening and subsequent failure of the joint as reported to be caused by the wear debris, is addressed and lessened. As well, tribological characteristics of the joint can be substantially improved, and thus, longer-lasting articulations of the implanted joints can be achieved. In the case of hemi-joint implants, more pain-free joints can be achieved.

Numerous further advantages attend the invention.

DRAWINGS IN BRIEF

The drawings form part of the specification hereof. As concerns the drawings, which are not necessarily drawn to scale, the sole FIGURE illustrates, in partial or full cross-section, various distinct diamond coated joint implant embodiments of the invention, some of which are shown as being implanted in human bone stock. These include, in the top left corner, a modular shoulder humeral component implant; in the top right corner, a total knee implant; in the left central region, a conservative resurfacing total hip joint; in the right central region, a snap-fitting acetabular cup component for a total, conventional hip implant; and in the bottom right corner, a basal thumb joint.

Figure 7:
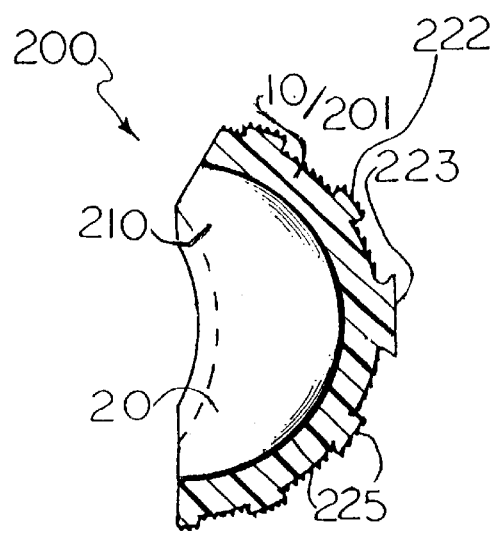
Figure 8:

In addition, FIGS. 6–8 show, in general, certain acetabular cups of the invention, each having a mountable back surface and a diamond or diamond-like coating on its articular surface, with FIG. 6 being a top view of such an acetabular cup;

FIG. 7 being a sectional view of such an acetabular cup, which, as otherwise would be in FIG. 3, is embodied as a plastic cup for total, resurfacing hip replacement; and FIG. 8 being a sectional view of such an acetabular cup, which, as in FIG. 4, is embodied as a snap-fitting plastic cup for total, conventional hip replacement.

DETAILED DESCRIPTION OF ILLUSTRATIVE EMBODIMENTS OF THE INVENTION

The invention can be further understood by the present detail which may be read in view of the drawings. The same is to be taken in an illustrative and not necessarily limiting sense.

The diamond or diamond like coated joint implant of the invention can be based upon a metal or other suitable support material, which is coated with a diamond and/or diamond like substance. For instance, a suitable biocompatible metal such as titanium or a cobalt-containing alloy can be treated by methods known in the art of diamond coated mechanical bearing manufacture such as those which include laser impingement techniques in order to provide a diamond coating on the outer surface of the underlying metal surface. The support may be ceramic or a plastic, for example, ZIRALLOY ceramic or UHMWPE, or, for instance, polyurethane, and so forth and the like. The coating may be applied by any suitable method or process, to include by such methods or processes as high pressure, high temperature (HPHT) techniques; conventional flame; torch; alternating current (AC) and direct current (DC) arc; arc jets; hot filament; radiofrequency (RF) chemical vapor deposition (CVD); electron-cyclotron resonance (ECR); enhanced CVD; supersonic beam; ion beam; laser ablation; and laser plasma-assisted synthesis techniques. Beneficially, however, the coating is generally transitional in nature; in other words, it is generally layered: a first layer made of carbon-containing moieties or carbon is attached directly to the metal and made integral therewith; intermediate layer(s) of carbon-containing moieties or carbon is(are) attached directly to the first layer and made integral therewith; and the outermost layer(s), which is made integral with the outermost intermediate layer, become(s) diamond-like carbon. The transitional layers may be considered to be chemically bonded through high energy chemical bonds, and thus integral one with another and with the underlying metal support. The outer diamond coating layer, and in particular, in the transitional all metal or alloy to laser-induced attached compound to all diamond coating layer, may be exceedingly, if not microscopically if not submicroscopically, thin, even in layers as thin as molecular layers. Along these lines, transitional type coatings may be applied by a process generally known as a QQC process such as disclosed in U.S. Pat. Nos. 5,900,225; 5,731,046; 5,648,127; 5,643,641; 5,635,243; 5,620,754, 5,554,415 and/or 5,516,500, each of these patents being incorporated herein by reference, as well as are patents cited in and incorporated into the specifications whereof, which may include as appropriate U.S. Pat. Nos. 5,273,788; 5,236,545; 5,176,788; 5,154,945; 5,098,737; 5,094,915; 5,080,752; 5,066,515; 4,987,007; 4,986,214; 4,981,717; 4,954,365; 4,948,629; 4,874,596; 4,849,199; 4,522,680; as well as 5,139,591; 5,096,740; 5,080,753; 5,017,317; 4,892,751; 4,701,592 and 4,681,640; and, in addition, 5,260,009; 5,256,340; 5,248,456; 5,247,180; 5,236,637 and 5,130,111.

Preferably, the support, say, for illustrative purposes, a metal, ceramic or plastic, is first formed into a joint precursor having the basic shape of the joint implant, the final dimensions determined by the coating layer(s). However, the transitional coating can be so thin that it hardly changes the size of the implant foundation formed from the metal. With an underlying, foundational metal precursor and a diamond or diamond like coating such as this, the metal core can provide desired tensile strength for the implant. In addition, with the use of metal as a foundation, the joint implant can be made of less material than would be if made of a known ceramic, and thus, less bone needs to be resected. And so, bone can be conserved. The present coating provides an extraordinarily hard and exceedingly smooth surface for articulation with a receiving surface such as of polyethylene or polyurethane. Thus, the joint articulation surface lasts longer, and consequent wear-induced debris is reduced, especially in total joint implants. As well, tribological characteristics of the joint articulation can be improved to approximate those found in natural, normal joints. As an alternative, the diamond coated joint implant may be be made for implantation in a hemi-joint procedure such as a hip resurfacing operation using the natural acetabulum; in this case, decrease in post-operative discomfort results. As another alternative, "diamond on diamond" (to include one or more surface(s) of diamond like coating) joint articulating surfaces may be provided.

The diamond coated implant can comprise heads or other convex articulating surfaces and/or sockets or other concave articulating surfaces of any suitable joint. The coated articulating surface can be variable in contour. For example, ginglymous or enarthrodial type joints, to include of the knee, elbow, hip, shoulder, digits, and so forth can be provided.

With reference to the sole FIGURE, depicted implants 100 include an underlying supporting substrate component 10 and transitional layer with diamond or diamond like carbon coating surface 20, for example, biocompatible cobalt-containing alloy as the substrate for the shoulder, humeral component; conservative hip resurfacing, femoral component; knee, femoral component; and basal thumb joint implant. The heads may be modular such as where the head, which may be of any suitable material, say, the cobalt-containing alloy or a suitable ceramic, has a Morse or other suitable taper receiving bore into which a correspondingly appropriately tapered trunion is inserted, or another form of modularity may be provided, say, by threads, etc. The implant 100 can be made of a suitable plastic, for example, UHMWPE, for example, in an acetabular cup, for conventional or resurfacing hip replacement, say, the snap-fitting conventional acetabular cup depicted; and knee, tibial tray liner. The component shapes can be those known or developed in the art, and may be special. See, e.g., Townley, U.S. patent application Ser. Nos. 09/148,842; 09/160,746; and 09/352,472—the specifications of which are incorporated herein by reference.

Thus, for example, as in FIGS. 3 and 4 but especially 6–8, head-receiving acetabular cup 200 for a ball and socket joint replacement implant can have body 10/201 including a nonmetallic plastic substantially as soft as a polyethylene and/or a polyurethane, and concave articulating surface 210 with mountable back surface 220. The mountable back surface 220 can include small, widely dispersed elevation members 221 extending from the surface 220 to provide for an appropriately thick cement mantle intended to assure an optimally proficient, implant-stabilizing cement mantle which is universally consistent and technically routine to implant. Note, general cement mantle 9 (FIG. 3). Of course, the concave articulating surface 210 is adapted for articulating with a corresponding external articulating surface of a ball joint head of a ball and socket head-containing hip joint femoral component when the cup 200 and femoral component are suitably mounted in suitable receiving stock. Compare, FIG. 3. The cup 200 is made of the plastic such that it can provide a support and precursor for the concave articulating surface 210, wherein the surface 210 has diamond or diamond like coating 20. The plastic employed leaves an underlying nonconverted supporting substrate for the coating 20, which is transitional in nature with an outer diamond or diamond like coating layer and a transitional layer to said nonconverted supporting substrate plastic of said component with said concave articulating surface, and which is microscopically or submicroscopically thin. The spacer elevation members can include an elevated block or button 223 centrally positioned on and extending from the back surface 220; and a plurality of rectangularly-shaped members 222 in block form to provide a block top and side walls, with the block top having a series of grooves 225 thereon and the side walls 221 being angled such that the members 222 are dove tailed, with the members 222 oriented in a series of concentric rows in relation to the elevated block or button 223. There can be concentrically bordering each series of rows of rectangularly-shaped members areas of the back surface 220 having a series of grooves 225.

CONCLUSION

The present invention is thus provided. Various features, subcombinations and combinations of the invention can be employed with or without reference to other features, subcombinations or combinations, and numerous adaptations and modifications can be effected within its spirit, and literal claim scope of which is particularly pointed out and distinctly claimed as follows.

What is claimed is:

1. A diamond or diamond like coated joint implant ensemble, which comprises:
    a first implant component including a nonmetallic plastic selected from the group consisting of a polyethylene and a polyurethane, and having a first articulating surface with a microscopic or submicroscopic coating that embraces an outer diamond or diamond like layer and a transitional layer on an underlying non-converted supporting substrate of said plastic; and a second implant component including a biocompatible material selected from the group consisting of a metal and a ceramic, and having a second articulating surface of said biocompatible material for articulating with said first articulating surface.

2. The implant ensemble of claim 1, wherein said biocompatible material has a diamond or diamond like coating on said second articulating surface.

3. The implant ensemble of claim 2, wherein said plastic is the polyethylene.

4. The implant ensemble of claim 3, which is for a ginglymous type joint.

5. The implant ensemble of claim 2, wherein said plastic is the polyurethane.

6. The implant ensemble of claim 1, wherein said plastic is the polyethylene.

7. The implant ensemble of claim 6, which is for an enarthrodial type joint.

8. The implant ensemble of claim 1, wherein said plastic is the polyurethane.

9. The implant ensemble of claim 7, which is for a ginglymous type joint.

10. The implant ensemble of claim 8, which is for an enarthrodial type joint.

11. The implant ensemble of claim 1, which is for a ginglymous type joint.

12. The implant ensemble of claim 1, which is for an enarthrodial type joint.

13. A component part for a total joint replacement implant, which component part includes a nonmetallic plastic selected from the group consisting of a polyethylene and a polyurethane, and has a concave articulating surface with a microscopic or submicroscopic coating that embraces an outer diamond or diamond like layer and a transitional layer on an underlying non-converted supporting substrate of said plastic.

14. The component part of claim 13, which is selected from the group consisting of a socket for an enarthrodial joint implant, and a tibial tray liner.

15. The component part of claim 14, which is an acetabular cup that is adapted for a conservative, resurfacing hip replacement implant.

16. The component part of claim 14, which is an acetabular cup that is adapted for a total, conventional hip replacement implant.

17. The component part of claim 14, which is the tibial tray liner.

18. The component part of claim 13, wherein said plastic is the polyethylene.

19. The component part of claim 13, wherein said plastic is the polyurethane.

20. A head-receiving acetabular cup for a ball and socket joint replacement implant, which cup comprises:

a body that includes a nonmetallic plastic selected from the group consisting of a polyethylene and a polyurethane;

a concave articulating surface with a microscopic or submicroscopic coating that embraces an outer diamond or diamond like layer and a transitional layer on an underlying non-converted supporting substrate of said plastic; and a mountable back surface wherein said mountable back surface includes small, widely dispersed elevation members extending from the back surface to provide for an appropriately thick cement mantle that is intended to assure an optimally proficient, implant-stabilizing cement mantle which is universally consistent and technically routine to implant, said concave articulating surface adapted for articulating with a corresponding external articulating surface of a ball joint head of a ball and socket head-containing hip joint femoral component when said cup and corresponding component are suitably mounted in suitable receiving stock.

21. The acetabular cup of claim 20, wherein said spacer elevation members include:

an elevated block or button centrally positioned on and extending from the back surface; and a plurality of rectangularly-shaped members in block form to provide a block top and side walls, said block top having a series of grooves thereon, said side walls being angled such that said members are dove tailed, and said plurality of members oriented in a series of concentric rows in relation to said elevated block or button; and there are, concentrically bordering each series of rows of rectangularly-shaped members, areas of the back surface having a series of grooves.

22. The cup of claim 20, wherein said plastic is UHMWPE.

* * * * *

UNITED STATES PATENT AND TRADEMARK OFFICE
CERTIFICATE OF CORRECTION

PATENT NO.    : 6,626,949 B1
DATED         : September 30, 2003
INVENTOR(S)   : Charles O. Townley It is certified that error appears in the above-identified patent and that said Letters Patent is hereby corrected as shown below:

<u>Column 2,</u>
Lines 14-25, replace the paragraph with the following:

The drawings form part of the specification hereof. As concerns the drawings, which are not necessarily drawn to scale, the figures illustrate, in partial or full cross-section, various distinct diamond coated joint implant embodiments of the invention, some of which are shown as being implanted in human bone stock. These include the following:

FIG. 1, which depicts a modular shoulder humeral component implant;

FIG. 2, which depicts a total knee implant ensemble;

FIG. 3, which depicts a conservative resurfacing total hip joint implant ensemble;

FIG. 4, which depicts a snap-fitting acetabular cup component for a total, conventional hip implant; and FIG. 5, which depicts a basal thumb joint implant.

<u>Column 3, line 62 to Column 4, line 16,</u>
Replace the paragraph with the following:

With reference to the figures, depicted implants 100 include an underlying supporting substrate component 10 and transitional layer with diamond or diamond like carbon coating surface 20, for example, biocompatible cobalt-containing alloy as the substrate for the shoulder, humeral component (FIG. 1); conservative hip resurfacing, femoral component (FIG. 3, bottom); knee, femoral component (FIG. 2, top); and basal thumb joint implant (FIG. 5). The heads may be modular such as where the head, which may be of any suitable material, say, the cobalt-containing alloy or a suitable ceramic, has a Morse or other suitable taper receiving bore into which a correspondingly appropriately tapered trunion is inserted, or another form of modularity may be provided, say, by threads, etc. The implant 100 can be made of a suitable plastic, for example, UHMWPE, for example, in an acetabular cup,

UNITED STATES PATENT AND TRADEMARK OFFICE
CERTIFICATE OF CORRECTION

PATENT NO.    : 6,626,949 B1
DATED         : September 30, 2003
INVENTOR(S)   : Charles O. Townley It is certified that error appears in the above-identified patent and that said Letters Patent is hereby corrected as shown below:

Column 3, line 62 to Column 4, line 16, cont'd,

```
for conventional or resurfacing hip replacement, say, the
snap-fitting conventional acetabular cup depicted (FIG. 3, top;
FIG. 4); and knee, tibial tray liner (FIG. 2, bottom).  The
component shapes can be those known or developed in the art, and
may be special.  See, e.g., Townley, U.S. patent application Nos.
09/148,842;  09/160,746; and 09/352,472 -- the specifications of
which are incorporated herein by reference.
```

Signed and Sealed this

Twentieth Day of January, 2004

JON W. DUDAS
*Acting Director of the United States Patent and Trademark Office*